United States Patent
Duflot

(10) Patent No.: US 8,865,948 B2
(45) Date of Patent: Oct. 21, 2014

(54) METHOD FOR MANUFACTURING HIGH-PURITY SORBITOL SYRUPS FROM SUCROSE AND USES THEREOF

(71) Applicant: Roquette Freres, Lestrem (FR)

(72) Inventor: Pierrick Duflot, La Couture (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 13/858,498

(22) Filed: Apr. 8, 2013

(65) Prior Publication Data
US 2013/0225874 A1 Aug. 29, 2013

Related U.S. Application Data

(63) Continuation of application No. PCT/FR2011/052345, filed on Oct. 7, 2011.

(30) Foreign Application Priority Data

Oct. 8, 2010 (FR) ...................................... 1058189

(51) Int. Cl.
*C07C 29/141* (2006.01)
*C07C 29/56* (2006.01)

(52) U.S. Cl.
CPC ............... *C07C 29/141* (2013.01); *C07C 29/56* (2013.01)
USPC ........................................................ 568/863

(58) Field of Classification Search
CPC .............................. C07C 29/141; C07C 29/56
USPC ........................................................ 568/863
See application file for complete search history.

(56) References Cited

U.S. PATENT DOCUMENTS

| | | | |
|---|---|---|---|
| 2,985,589 A | 5/1961 | Broughton et al. |
| 3,044,904 A | 7/1962 | Serbia |
| 3,416,961 A | 12/1968 | Mountfort et al. |
| 3,686,117 A | 8/1972 | Lauer et al. |
| 3,692,582 A | 9/1972 | Melaja |
| 4,157,267 A | 6/1979 | Odawara et al. |
| 4,182,633 A | 1/1980 | Ishikawa et al. |
| 4,226,977 A | 10/1980 | Neuzil et al. |
| 4,267,054 A | 5/1981 | Yoritomi et al. |
| 4,293,346 A | 10/1981 | Landis et al. |
| 4,322,569 A | 3/1982 | Chao et al. |
| 4,412,866 A | 11/1983 | Schoenrock et al. |
| 4,422,881 A | 12/1983 | Devos et al. |
| 2003/0175219 A1 | 9/2003 | Francois |

FOREIGN PATENT DOCUMENTS

| | | |
|---|---|---|
| CA | 1311503 | 6/1985 |
| CN | 1995367 A | 7/2007 |
| EP | 0 168 315 | 6/1985 |
| EP | 0 237 442 | 3/1986 |
| EP | 1 176 131 | 7/2001 |
| FR | 2 099 336 | 7/1971 |
| FR | 2 391 754 | 5/1978 |
| FR | 2 454 830 | 11/1980 |
| WO | WO 84/00778 | 3/1984 |
| WO | WO 03/007902 | 1/2003 |

OTHER PUBLICATIONS

Unknown "Sugar Alcohols (Polyols) & Polydextrose used as Sweetners in Foods" *Health Canada: Food and Nutrition*, Feb. 16, 2005, pp. 1-2, XP-002636221.
Unknown "Rice Sorbitol Syrup" *Brown Rice Syrups.com*, Nov. 14, 2006, pp. 1-2, XP-002636222.
Mao, L. et al. "Production of Sorbitol, High-Purity Fructose Syrup and Vitamin C by Sucrose" *Sugarcane Industry*, Dec. 31, 1989, pp. 38-44.
Zhang, Z. et al. "Deep Chemical Processing of Sucrose" *Sichuan Chemical Engineering and Corrosion Control*, Dec. 31, 1999, pp. 42-47.
Wang, C. et al. "Use of Chromatographic Separation Technology in Production of Sugar Alcohol" *Chinese Food Additives*, Dec. 31, 2007, pp. 1-3.

*Primary Examiner* — Elvis O Price
(74) *Attorney, Agent, or Firm* — Saliwanchik, Lloyd & Eisenschenk

(57) ABSTRACT

The invention relates to a method for manufacturing a sorbitol syrup having a total reducing sugar content no higher than 0.2% and mannitol content of less than 1%, with 70 wt % of dry matter. Said manufacturing method is characterized in that it includes the steps of: (a) hydrolyzing a solution of sucrose in a solution of invert sugars, (b) separating the solution of invert sugar by simulated moving bed chromatography into, on the one hand, a dextrose syrup having at least 99.3%, preferably 99.4%, more preferably at least 99.5%, and even more preferably 99.7% of dextrose content and, on the other hand, a fructose syrup having at least 90%, preferably 92% of fructose content, and (c) hydrogenating said dextrose syrup into a sorbitol syrup having a reducing sugar content no higher than 0.2% and a mannitol content of less than 1%, with 70 wt % of dry matter.

13 Claims, No Drawings

METHOD FOR MANUFACTURING HIGH-PURITY SORBITOL SYRUPS FROM SUCROSE AND USES THEREOF

CROSS-REFERENCE TO RELATED APPLICATION

This application is a continuation of International Application No. PCT/FR2011/052345, filed Oct. 7, 2011.

FIELD OF THE INVENTION

The subject of the present invention is a method for manufacturing high-purity sorbitol syrups and derivatives thereof from sucrose.

Its subject is more specifically a method for manufacturing high-purity sorbitol syrups from sucrose, said method being free of any crystallization step.

PRIOR ART

The industrial importance of sorbitol is well known, in particular in fields such as pharmacy, beauty care, food and chemistry. It is in particular used in syrup form for its excellent crystallization capacity, and its humectant and cryoprotectant properties. In powder form, sorbitol is widely used in tablets and chewing gums because of its very good compressibility and its cooling effect.

Sorbitol of high purity is generally obtained by hydrogenation of pure dextrose. Dextrose, or D-glucose, is traditionally obtained by crystallization of a glucose syrup, which constitutes the result of hydrolysis of starch which is a glucose polymer and represents the polysaccharide that is the energy reserve for many plants.

Another polysaccharide that is very widespread in the plant kingdom is sucrose. It is present in a high concentration in beet and sugar cane in particular.

Sucrose consists of a molecule of glucose and a molecule of fructose bound together by a β 1→2 bond. This bond is easily hydrolyzed under the effect of acids or enzymes such as yeast invertase for example. It is therefore easy to obtain, from sucrose, solutions commonly designated by the name "invert sugar" which contain dextrose and fructose in substantially equimolar quantities.

Accordingly, although sucrose is an abundant and inexpensive raw material, it is easy to understand why it is not generally used as raw material allowing the mass production of dextrose syrups of high purity, such a production being unavoidably linked to the simultaneous production, in a substantially equivalent quantity, of fructose.

It is however known to industrially separate the dextrose and fructose contained in solutions of invert sugar, especially by chromatography on an ion-exchange resin. This method makes it possible to obtain, on the one hand, a fructose-rich fraction and, on the other hand, a glucose-rich fraction.

The chromatographic separation step is generally carried out, in a manner well-known to a person skilled in the art, batchwise or continuously (simulated moving bed), on adsorbents of the type comprising strongly acidic, cationic resins loaded with alkali or alkaline-earth metal ions, or of the type comprising zeolites loaded with ammonium, sodium, potassium, calcium, strontium or barium ions. Examples of such chromatographic methods of separation are described in U.S. Pat. No. 3,044,904, U.S. Pat. No. 3,416,961, U.S. Pat. No. 3,692,582, FR 2 391 754, FR 2 099 336, U.S. Pat. No. 2,985,589, U.S. Pat. No. 4,226,977, U.S. Pat. No. 4,293,346, U.S. Pat. No. 4,157,267, U.S. Pat. No. 4,182,633, U.S. Pat. No. 4,412,866 and U.S. Pat. No. 4,422,881.

However, in such methods, the glucose fraction recovered at the end of the chromatography step has a relatively low purity and it is then essential to carry out a step for purifying said glucose fraction in order to obtain a glucose solution of high purity. The manufacture of sorbitol of high purity therefore requires, prior to the step of hydrogenation of D-glucose to sorbitol, at least two steps: a step of separating glucose and fructose and a step of purifying the glucose fraction.

By way of example, the applicant has in particular developed a method for producing sorbitol of high purity involving a chromatography step on cation-exchange resins followed by a step of purifying the glucose fraction by crystallization. Said method is described in the document EP 0 237 442. According to a preferred embodiment, the chromatographic separation step is carried out using the method and apparatus described in U.S. Pat. No. 4,422,881 and the corresponding patent FR 2 454 830, of which the applicant company is proprietor.

It is to the applicant's credit to have succeeded in manufacturing a high-purity sorbitol syrup from sucrose, the method for manufacturing sorbitol of high purity involving a chromatography step not followed by an additional purification step such as a crystallization step. Thus, by virtue of the method according to the invention, it is possible to manufacture sorbitol of high purity from sucrose in a simplified manner involving only three main steps: (a) a step of hydrolyzing sucrose to glucose and fructose, (b) a step of separating the glucose and fructose fractions and (c) a step of hydrogenating the glucose fraction.

SUMMARY OF THE INVENTION

The present invention therefore consists of a method for manufacturing a sorbitol syrup having a total reducing sugar content of less than or equal to 0.2% and a mannitol content of less than 1%, with 70 wt % of dry matter (DM) from sucrose, characterized in that it comprises the steps consisting in:

a. hydrolyzing a solution of sucrose to a solution of invert sugar, b. separating the solution of invert sugar by simulated moving bed chromatography into
    a dextrose syrup having at least 99.3%, preferably 99.4%, more preferably 99.5%, and even more preferably 99.7% of dextrose content,
    a fructose syrup having at least 90%, preferably 92%, of fructose content, c. hydrogenating, preferably directly after step (b), said dextrose syrup into a sorbitol syrup having a total reducing sugar content of less than or equal to 0.2% and a mannitol content of less than 1%, with 70 wt % of DM.

DETAILED DESCRIPTION

The subject of the present invention is a method for manufacturing high-purity sorbitol syrups from sucrose, said method, comprising three main steps of hydrolysis (a), separation by chromatography (b) and hydrogenation (c), is free of any crystallization step. According to a preferred mode of the present invention, step (b) of separation by simulated moving bed chromatography is performed in the Improved SMB mode, said step (b) preferably has moreover a glucose recovery yield greater than 85%, preferably greater than 87% and even more preferably greater than 88%.

The method in accordance with the invention may be carried out with the aid of an installation essentially comprising:

a chamber A in which the inversion of sucrose is carried out, a chamber B for chromatographic separation, and a chamber C in which the syrup enriched with glucose, collected after the chromatography step, is hydrogenated into a sorbitol syrup.

Various filtration, decoloration and/or demineralization systems which are customarily connected to these chambers and which are well known to a person skilled in the art may complete the installation in accordance with the invention.

More precise information will be given below, as a guide, as regards the assembly and operation of these various chambers.

The chamber A receives the sucrose dissolved in an aqueous solution containing a dry matter content generally between 30 and 70% approximately. The sucrose is then subjected to an inversion step, that is to say a hydrolysis into an invert sugar syrup. In the present application, the expression "invert sugar" is understood to mean a substantially equimolar mixture of glucose and fructose obtained by hydrolysis of sucrose. The hydrolysis may be carried out by any enzymatic or chemical method well-known to a person skilled in the art. According to a preferred embodiment, the inversion may be carried out by the hydrolyzing action of yeast invertase, for example Invertase® marketed by the company NOVO NORDISK, Paris, France, in order to obtain a specific optical rotation of about −19 Deg.

The inversion performed in the chamber A may be of the continuous or batch type, but advantageously consists of a continuous reactor containing the enzyme in immobilized form or alternatively a strong cationic resin in hydrogen form.

Step (b) of separation by simulated moving bed chromatography of the solution of invert sugar is carried out in the chamber B. The chamber B is designed and exploited so as to obtain, on the one hand, a "Glucose" fraction which is a dextrose-rich syrup preferably containing at least 99.3%, preferably 99.4%, more preferably 99.5%, and more preferably still 99.7% of dextrose and, on the other hand, a "Fructose" fraction consisting of a fructose-rich syrup, containing a glucose content that is as low as possible.

The chromatographic separation step is carried out in an SMB (Simulated Moving Bed) assembly of one or more simulated moving beds filled with ion-exchange resins, for example known under the reference DIAION UBK 535K, Resindion S.R.L., Mitsubishi Chemical Corporation, Binasco, Italy. This assembly preferably works in the ISMB mode (Improved SMB mode), which is the subject in particular of the documents EP 1352967 and EP 663224. This technique is better compared with a conventional SMB assembly, which is well known to a person skilled in the art, because it makes it possible to obtain higher concentrations while avoiding having to recirculate the permeate during the fractionation. Furthermore, it makes it possible to work with a higher volumetric charge, a smaller resin volume compared with the conventional SMB technique and a lower water and energy consumption. The ISMB chromatography exploitation mode makes it possible to maintain, inside each column, a constant profile for distribution and concentration of the various fractions and consequently promotes the separation thereof.

Chromatography with a limited number of columns, for example 4, is preferably used. Thus, according to a preferred mode of the present invention, four columns mounted in series and forming an SMB 4 assembly are used.

The chromatography support is preferably a cationic gel resin in calcium form. This resin is preferably used among the alkali and alkaline-earth metal cations. A low degree of crosslinking and a small particle size (220 μm diameter on average) with a high degree of uniformity (over 85% of the resin beads between 200 and 400 μm) will be preferred in order to improve the separation. According to a preferred embodiment, a strong acidic cationic ion exchange resin such as the resin FINEX CS 104 GC is used.

The ISMB method according to the invention makes it possible to obtain a "Glucose" fraction having a minimum glucose purity of 96% with a glucose recovery yield greater than 85%, preferably greater than 87% and even more preferably greater than 88%. According to the present invention, the expression "glucose recovery yield" is understood to mean the following quotient:

$$P_{glucose} = (\text{DM of glucose in the Glucose fraction})/(\text{DM of glucose at the chromatography inlet})$$

The chamber C is fed from the glucose-enriched fraction derived from the chamber B. Said Glucose fraction, derived from the chromatography step, is hydrogenated in the chamber C in a conventional manner. According to a preferred mode, the Glucose fraction is hydrogenated at 45% of DM under a hydrogen pressure of 60 bar. During hydrogenation, the pH decreases slowly to a low value of about 4.5. According to a preferred mode of the invention, the pH is kept low (about 4.5) for more than 15 minutes, preferably for more than 20 minutes in order to hydrolyze the residual traces of sucrose. The pH is then increased to 8, preferably by adding sodium hydroxide, preferably in the form of an aqueous sodium hydroxide solution, in order to end the hydrogenation up to a reducing sugar content of less than or equal to 0.2%, preferably less than or equal to 0.1% on a dry basis.

According to a preferred mode of the invention, the syrup is then evaporated to a dry matter (DM) content greater than 50%.

At the end of the method according to the invention, an extremely pure sorbitol syrup is obtained which may be completely dehydrated in order to form sorbitol powder. According to a preferred mode of the invention, a syrup is obtained whose final analysis, according to the Bertrand gravimetric method, shows a total reducing sugar level of less than or equal to 0.2%, preferably of less than or equal to 0.1%, and a mannitol level of less than 1%, with a 70 wt % of DM. HPLC analysis on a dry basis gives a sorbitol content greater than 97%, preferably greater than 98%.

According to a particular embodiment of the invention, the glucose-enriched syrup, derived from the chromatography step, is purified in a manner well known to a person skilled in the art, for example by decoloration and/or demineralization.

The sorbitol obtained at the end of the method according to the invention finds application in the chemical, pharmaceutical, beauty care and food industries in particular. Thus, the subject of the present invention is also the use of a sorbitol syrup obtained or capable of being obtained using the method according to the invention for the manufacture of foods, pharmaceutical or beauty care products.

Sorbitol is also used in paper making and foundry and represents the raw material for the synthesis of vitamin C.

Furthermore, the sorbitol obtained according to the invention may be used to make anhydrides, ethers or esters which find application in the plastics or detergent industries, for example.

Finally, the Fructose fraction recovered in step (b) and consisting of a fructose-enriched syrup, containing a glucose content which is as low as possible, may be advantageously used for human consumption, in particular as raw material for the preparation of mannitol, or may be recycled with a glucose isomerase in order to prepare an invert sugar.

The invention will be understood more clearly with the aid of the following examples, which are not intended to be limiting and only represent certain embodiments according to the invention.

EXAMPLE 1

Production, According to the Invention, of Sorbitol of High Purity from Sucrose

The inversion of sucrose is carried out in a 100 m³ tank (chamber A) in the following manner:

The sucrose is dissolved in water at 50% of DM and the solution is heated to 60° C. The pH is adjusted to 4.75. An enzymatic solution of invertase marketed by the company NOVO under the name Invertase®, is then added in an amount of 20 g per ton of sucrose. After 20 hours of inversion, the invert syrup obtained has the following composition (analysis by high-performance liquid chromatography): 51.2% of glucose, 48.7% of fructose and 0.1% of other monosaccharides.

The invert syrup is then demineralized and then concentrated to a dry matter content of 55% before being conveyed to the sequential separation continuous chromatography chamber ISMB marketed by the company EURODIA. Said chromatography chamber having a volume of 28 m³ is then equipped with resins FINEX CS 104 GC with a mean diameter of 220 μm.

The chromatography is fed with, on the one hand, the invert syrup at a flow rate of 1.9 m³/h, that is 1.27 T sec/h and, on the other hand, demineralized water at a flow rate of 2.88 m³/h. Under these conditions, the chromatography is fed in an amount of 55% of DM.

The chromatography is carried out so as to extract the glucose in an amount of 99.4%. The Glucose fraction is then extracted at a flow rate of 2.86 m³/h, that is 0.58 T sec/h and has the following composition: glucose 99.4%, fructose 0.5% and others 0.1%.

Under these conditions, the fructose-enriched fraction has a glucose titer of 9.9%. Thus, the Fructose fraction is extracted at a flow rate of 1.92 m³/h, that is 0.69 T sec/h and has the following composition: glucose 9.9% and fructose 90.1%.

The glucose-enriched syrup (or Glucose fraction), derived from the chromatography step, is purified in a conventional manner by decoloration and/or demineralization. It has a glucose titer of 99.4% (on the basis of the DM) and does not contain high-molecular weight polysaccharides.

The Glucose fraction is hydrogenated at 45% of DM, 140° C., at a hydrogen pressure of 60 bar. During the hydrogenation, the pH decreases slowly to 4.5. The pH is left at a value of 4.5 for 20 minutes in order to hydrolyze the residual traces of sucrose. The pH is then increased to 8 by the addition of sodium hydroxide in order to end the hydrogenation until a reducing sugar content of less than 0.1% on a dry basis is obtained.

The hydrogenated syrup is then purified by demineralization and treatment on activated carbon and is evaporated to 70% of DM. A hydrogenated dextrose syrup or sorbitol syrup having a total reducing sugar level equal to 0.1% at 70% of DM is thus obtained. Said sorbitol syrup has a sorbitol content of 98.9%, a mannitol content of 0.7%, an iditol content of 0.3% (analysis on a dry basis). The balance for 100% is analyzed as products of cracking and other constituents.

EXAMPLE 2

Production of Sorbitol of High Purity from Glucose Monohydrate

A solution of glucose obtained from the remelting of a dextrose monohydrate LYCADEX® marketed by the applicant company, having a specific optical rotation of 53.1 Deg is brought to 45% of DM in an 18 m³ hydrogenator. The temperature is brought to 140° C. and the hydrogen pressure to 60 bar.

The pH decreases slowly to a value of 4.5. At this moment, the pH is increased to 8 by the addition of sodium hydroxide. When the reducing sugar content is less than 0.1% on a dry basis, the reaction is stopped. The sorbitol syrup thus obtained is then purified by demineralization and treatment on activated carbon. Said sorbitol syrup is then evaporated to 70% of DM. A sorbitol syrup having a total reducing sugar level equal to 0.18% at 70% of DM is thus obtained. Said sorbitol syrup has a sorbital content of 98.6%, a mannitol content of 0.4%, an iditol content of 0.3%, a hydrogenated $DP_2$ content of 0.2% (analysis on a dry basis). The balance for 100% is analyzed as products of cracking and other constituents.

The method according to the invention, as described in Example 1, makes it possible to obtain, from sucrose, a sorbitol syrup with a purity equivalent to the reference method for producing sorbitol of high purity described above.

EXAMPLE 3

Production of Sorbitol from Sucrose Using a Conventional SMB Chromatography Method The inversion of sucrose is carried out as described in Example 1. After the inversion step, the invert syrup obtained has the following composition (analysis by high-performance liquid chromatography): 51.2% of glucose, 48.7% of fructose and 0.1% of other monosaccharides.

The invert syrup is then demineralized and then concentrated to a dry matter content of 55% before being conveyed to a conventional SMB chromatography chamber operating according to the teaching of patent FR 2 550 462. Said chromatography chamber has a volume of 80 m³ and is equipped with 10 plates and with FINEX CS 104 GC resin having a mean diameter of 220 μm.

The SMB chromatography is fed with, on the one hand, the invert syrup at a flow rate of 5.8 m³/h, that is 3.9 T sec/h and, on the other hand, demineralized water at a flow rate of 12 m³/h. Under these conditions, the chromatography is fed with an amount of 55% of DM.

The chromatography is carried out so as to extract the glucose in an amount that is as high as possible, namely in an amount of 97.8%. The Glucose fraction is thus extracted at a flow rate of 10.95 m³/h, that is 1.7 T sec/h, and has a DM of 14.5% and the following composition: glucose 97.8%, fructose 2.1% and others 0.1%.

Under these conditions, the fructose-enriched fraction has a titer of 14.1% glucose. Thus, the Fructose fraction is extracted at a flow rate of 6.85 m³/h, that is 2.2 T sec/h, and has a DM of 29.5% and the following composition: glucose 14.1% and fructose 85.9%.

The glucose-enriched syrup (or Glucose fraction), derived from the chromatography step, is purified in a conventional manner by decoloration and/or demineralization; it has a titer of 97.8% glucose (on the basis of the DM) and does not contain high molecular weight polysaccharide.

The glucose-enriched syrup is hydrogenated in the same manner as in Example 1. In accordance with Example 1, the hydrogenated syrup is then purified and is evaporated to 70% of DM. A sorbitol syrup is thus obtained having a total reducing sugar level equal to 0.11% at 70% of DM. Said sorbitol syrup has a sorbitol content of 97.6%, a mannitol content of 1.8%, an iditol content of 0.3% (analysis on a dry basis). The balance for 100% is analyzed as cracking products and other constituents.

Accordingly, a conventional SMB chromatography method, that is not in accordance with the invention and not followed by a Glucose fraction purification step such as a crystallization does not make it possible to obtain a sorbitol of high purity from sucrose, i.e. a sorbitol having a reducing sugar content of less than or equal to 0.2% reducing sugars.

EXAMPLE 4

Production of Sorbitol from Sucrose Using a Conventional SMB Chromatography Method Followed by a Crystallization Step The procedure is carried out in the same manner as in Example 3 up to the production of the glucose-enriched syrup (or Glucose fraction) which is obtained from the chromatography step. The glucose-enriched syrup is then purified in a conventional manner by decoloration and/or demineralization; it has a titer of 97.8% glucose (on the basis of the DM) and does not contain high molecular weight polysaccharide.

The glucose-enriched and purified syrup is then concentrated to 74% of DM and placed in a 30 m$^3$ batch crystallizer. To the purified syrup there is added 5% seed crystals (percentage on DM). The crystallizer is cooled from 50° C. to 25° C. over 48 hours. The massecuite obtained during the crystallization method is separated in a centrifugal drainer. After washing, the crystals have a specific optical rotation equal to 52.8 Deg. The crystals, analyzed by HPLC, have a glucose content equal to 99.8% and a fructose content equal to 0.2%. The crystal yield on the dry matter used in crystallization is 53%. The mother liquors have a glucose content of 95.7% and a fructose content of 4%. The balance for 100% consists of sucrose and traces of hydroxy-methyl-furfuran.

The crystals are dissolved and hydrogenated in the same manner as in Example 3. After purification and evaporation, a sorbitol syrup is thus obtained which has a total reducing sugar level equal to 0.07% at 70% of DM. Said sorbitol syrup has a sorbitol content of 99.1%, a mannitol content of 0.4%, an iditol content of 0.3% (analysis on a dry basis). The balance for 100% is analyzed as products of cracking and other constituents.

Accordingly, using a conventional SMB chromatography method not in accordance with the invention, a purification step such as a step of crystallization of the Glucose fraction derived from SMB chromatography is essential in order to obtain a sorbitol of high purity from sucrose, i.e. a sorbitol containing 0.2% of total reducing sugars.

I claim:

1. A method for manufacturing a sorbitol syrup having a total reducing sugar content of less than or equal to 0.2% and a mannitol content of less than 1%, with 70 wt% of dry matter from sucrose, wherein said method comprises the steps of:
    a) hydrolyzing a solution of sucrose to a solution of invert sugar,
    b) separating the solution of invert sugar by simulated moving bed chromatography into
        a dextrose syrup having at least 99.3% dextrose content,
        a fructose syrup having at least 90% fructose content, and
    c) hydrogenating said dextrose syrup into a sorbitol syrup having a total reducing sugar content of less than or equal to 0.2% and a mannitol content of less than 1%, with 70 wt% of dry matter.

2. The method according to claim 1, wherein said method is free of any crystallization step.

3. The method according to claim 1, wherein said separation by simulated moving bed chromatography is performed in the Improved SMB mode.

4. The method according to claim 1, wherein said separation by simulated moving bed chromatography has a glucose recovery yield greater than 85%.

5. The method according to claim 1, wherein the pH at the end of step (c) is left at 4.5 for more than 15 minutes or more than 20 minutes.

6. The method according to claim 1, wherein said method consists of the steps:
    a) hydrolyzing a solution of sucrose to a solution of invert sugar,
    b) separating the solution of invert sugar by simulated moving bed chromatography into
        a dextrose syrup having at least 99.3% dextrose content,
        a fructose syrup having at least 90% fructose content, and
    c) hydrogenating said dextrose syrup into a sorbitol syrup having a total reducing sugar content of less than or equal to 0.2% and a mannitol content of less than 1%, with 70 wt% of dry matter.

7. The method according to claim 1, wherein said hydrogenating step is performed directly after step (b).

8. The method according to claim 6, wherein said hydrogenating step is performed directly after step (b).

9. The method according to claim 1, wherein the dextrose syrup has at least 99.5% dextrose content, at least 99.7% dextrose content or at least 99.4% dextrose content.

10. The method according to claim 1, wherein the fructose syrup has at least 92% fructose content.

11. The method according to claim 4, wherein the glucose recovery yield is greater than 87% or 88%.

12. The method according to claim 6, wherein the dextrose syrup has at least 99.5% dextrose content, at least 99.7% dextrose content or at least 99.4% dextrose content.

13. The method according to claim 6, wherein the fructose syrup has at least 92% fructose content.

* * * * *